(12) United States Patent
     Gilstrap et al.

(10) Patent No.: US 12,667,426 B2
(45) Date of Patent: Jun. 30, 2026

(54) LOCALIZATION DEVICE, DELIVERY DEVICES, SYSTEMS AND METHODS

(71) Applicant: Cianna Medical, Inc., Aliso Viejo, CA (US)

(72) Inventors: David Gilstrap, South Jordan, UT (US); Amber Velasco, South Jordan, UT (US); Gregory R. McArthur, Sandy, UT (US); Matthew Bainsmith, South Jordan, UT (US)

(73) Assignee: Cianna Medical, Inc., Aliso Viejo, CA (US)

( * ) Notice: Subject to any disclaimer, the term of this patent is extended or adjusted under 35 U.S.C. 154(b) by 169 days.

(21) Appl. No.: 17/934,285

(22) Filed: Sep. 22, 2022

(65) Prior Publication Data

US 2023/0098300 A1     Mar. 30, 2023

Related U.S. Application Data

(60) Provisional application No. 63/248,163, filed on Sep. 24, 2021.

(51) Int. Cl.
     *A61B 10/02*     (2006.01)
     *A61B 34/20*     (2016.01)
(52) U.S. Cl.
     CPC .......... *A61B 34/20* (2016.02); *A61B 10/0233* (2013.01); *A61B 2034/2051* (2016.02)
(58) Field of Classification Search
     CPC ................ A61B 34/20; A61B 10/0233; A61B 2034/2051
     See application file for complete search history.

(56) References Cited

U.S. PATENT DOCUMENTS

| | | | | |
|---|---|---|---|---|
| 5,380,295 | A | * | 1/1995 | Vacca ................. A61M 5/5013 |
| | | | | 604/199 |
| 6,093,154 | A | | 7/2000 | Burek et al. |
| 2004/0059343 | A1 | * | 3/2004 | Shearer ................. A61F 2/1664 |
| | | | | 606/107 |

(Continued)

FOREIGN PATENT DOCUMENTS

| | | | |
|---|---|---|---|
| WO | 2020243470 A1 | 12/2020 | |

OTHER PUBLICATIONS

International Search Report and Written Opinion dated Jan. 10, 2023 for PCT/US2022/076860.
European Search Report dated Jul. 11, 2025. for EP22873858.9.

*Primary Examiner* — Amal Aly Farag
(74) *Attorney, Agent, or Firm* — Dorsey & Whitney LLP

(57)     ABSTRACT

Devices, systems, and methods used to deploy a localization device into a target lesion are disclosed. The system includes a delivery device configurable in a ready-to-deploy state and a deployed state. When the delivery device is in the ready-to-deploy state, biased engagement members are engaged with proximal detents of a handle of the delivery device. When the delivery device is in the deployed state, the biased engagement members are engaged with distal detents. The delivery device is transitioned from the ready-to-deploy state to the deployed state by distal displacement of a plunger relative to the handle. The localization device is deployed from a cannula of the delivery device into the target lesion when the delivery device transitions from the ready-to-deploy state to the deployed state.

10 Claims, 16 Drawing Sheets

(56) References Cited

U.S. PATENT DOCUMENTS

| | | | |
|---|---|---|---|
| 2007/0106108 A1* | 5/2007 | Hermann | A61N 5/1015 |
| | | | 600/7 |
| 2008/0139925 A1 | 6/2008 | Lubock et al. | |
| 2008/0255501 A1* | 10/2008 | Hogendijk | A61B 17/562 |
| | | | 604/60 |
| 2009/0209804 A1 | 8/2009 | Seiler et al. | |
| 2009/0247900 A1* | 10/2009 | Zimmer | A61B 10/0275 |
| | | | 600/564 |
| 2015/0201947 A1 | 7/2015 | Hill et al. | |
| 2016/0361088 A1* | 12/2016 | Maguire | A61B 17/3415 |
| 2017/0100203 A1 | 4/2017 | Field et al. | |
| 2017/0231716 A1 | 8/2017 | Ahari et al. | |
| 2017/0252124 A1* | 9/2017 | Greene | A61B 90/06 |
| 2018/0318037 A1* | 11/2018 | Tanghal | A61B 90/39 |
| 2019/0117112 A1 | 4/2019 | Rulkov et al. | |
| 2019/0150900 A1 | 5/2019 | Choung et al. | |
| 2020/0060726 A1 | 2/2020 | Campbell et al. | |
| 2020/0121414 A1 | 4/2020 | Springs et al. | |
| 2021/0030404 A1 | 2/2021 | Van Liere et al. | |
| 2021/0177523 A1* | 6/2021 | Ebrahimi | A61B 17/24 |
| 2021/0204832 A1 | 7/2021 | Chi Sing et al. | |
| 2021/0282754 A1* | 9/2021 | Nock | A61B 90/39 |

* cited by examiner

LOCALIZATION DEVICE, DELIVERY DEVICES, SYSTEMS AND METHODS

RELATED APPLICATIONS

This application claims priority to U.S. Provisional Application No. 63/248,163, filed on Sep. 24, 2021 and titled, "Localization Device, Delivery Devices, Systems and Methods," which is hereby incorporated by reference in its entirety.

TECHNICAL FIELD

The present disclosure relates generally to devices to treat lesions within organs. More specifically, the present disclosure relates to a delivery device for deployment of a localization device into a lesion of an organ.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
FIG. 1 is a perspective view of an embodiment of a localization device deployment system including a delivery device, a sheath introducer, a spacer and a localization device.

In certain instances, a lesion, such as a tumor, within a patient's body is biopsied to provide a tissue sample for analysis. The biopsy procedure can be accomplished utilizing magnetic resonance imaging (MRI) or stereotactic guidance to guide a biopsy device into the lesion. In some instances, the biopsy device is removed from the patient with the tissue sample as an introducer sheath of the biopsy device remains in place. A marker, such as a localization device, can be deployed into the lesion to identify a location of the lesion for subsequent procedures, such as surgical removal of the lesion, targeted radiation therapy, etc. The localization device can be deployed from a delivery device introduced into the lesion through the sheath introducer. This configuration combines two procedures into one to reduce procedural risks and costs.

Embodiments herein describe localization device delivery devices, systems, and methods to deploy a localization device into a target lesion. In one embodiment within the scope of this disclosure, the system includes a delivery device, a sheath introducer, and a localization device. The delivery device includes a handle to be gripped by a user, a cannula coupled to the handle, a plunger slidingly disposed within the handle, and a deployment rod coupled to the plunger and slidingly disposed within the cannula. The handle includes ready-to-deploy windows and deployed windows. The plunger includes biased members with catches that engage with the ready-to-deploy windows when the delivery device is in a ready-to-deploy state and engage with the deployed windows when the delivery device is in a deployed state. The cannula includes a retention tab to retain the localization device within the cannula and a window to confirm retention of the localization device within the cannula.

Methods of deploying a localization device within the scope of this disclosure may include positioning a distal portion of a delivery device within a target lesion, transitioning the delivery device from a ready-to-deploy state to a deployed state, wherein a plunger of the delivery device is displaced from engagement with a ready-to-deploy detent of the delivery device to engagement with a deployed detent of the delivery device, and deploying a localization device from the delivery device into the target lesion.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

FIG. 1 illustrates an embodiment of a localization device deployment system including a delivery device, a sheath introducer, and a localization device. FIGS. 2A, 2B, and 6-14 illustrate an embodiment of the delivery device in a ready-to-deploy state. FIGS. 3A and 3B illustrate an embodiment of the delivery device in a deployed state. FIGS. 4 and 15-22 illustrate an embodiment of a spacer of the deployment system. FIGS. 5A and 5B illustrate a method of use of the deployment system. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 illustrates a localization device deployment system (deployment system) 100 for deployment of a localization device including three broad groups of components; each group may have numerous subcomponents and parts. The four broad component groups are: a delivery device 110, a spacer 160, a localization device 180, and a sheath introducer 190. As illustrated in FIG. 1, the localization device 180 can include a body 181 and antennae 182 extending from opposing ends of the body 181. Electronics to allow the localization device 180 to be activated by an external signal, such as ultraviolet light, and to reflect a radar signal to an external receiver can be enclosed within the body 181. In other embodiments, the localization device 180 may be of any suitable type configured to transmit a signal to an external receiver. For example, the localization device 180 may actively or passively transmit the signal to the receiver.

The illustrated embodiment of the sheath introducer 190 includes a hub 191 disposed at a proximal end of a tubular sheath 192. The hub 191 can be of any various forms to facilitate manipulation of the sheath introducer 190 and to guide the delivery device 110 into the tubular sheath 192. A length of the tubular sheath 192 may vary depending upon the type of procedure the sheath introducer 190 is used for. For example, the length of the tubular sheath 192 can range between about 98 millimeters and 106 millimeters when the sheath introducer 190 is used for a stereotactic biopsy procedure and can be about 88 millimeters when the sheath introducer 190 is used for an MRI biopsy procedure.

Figure 2A:
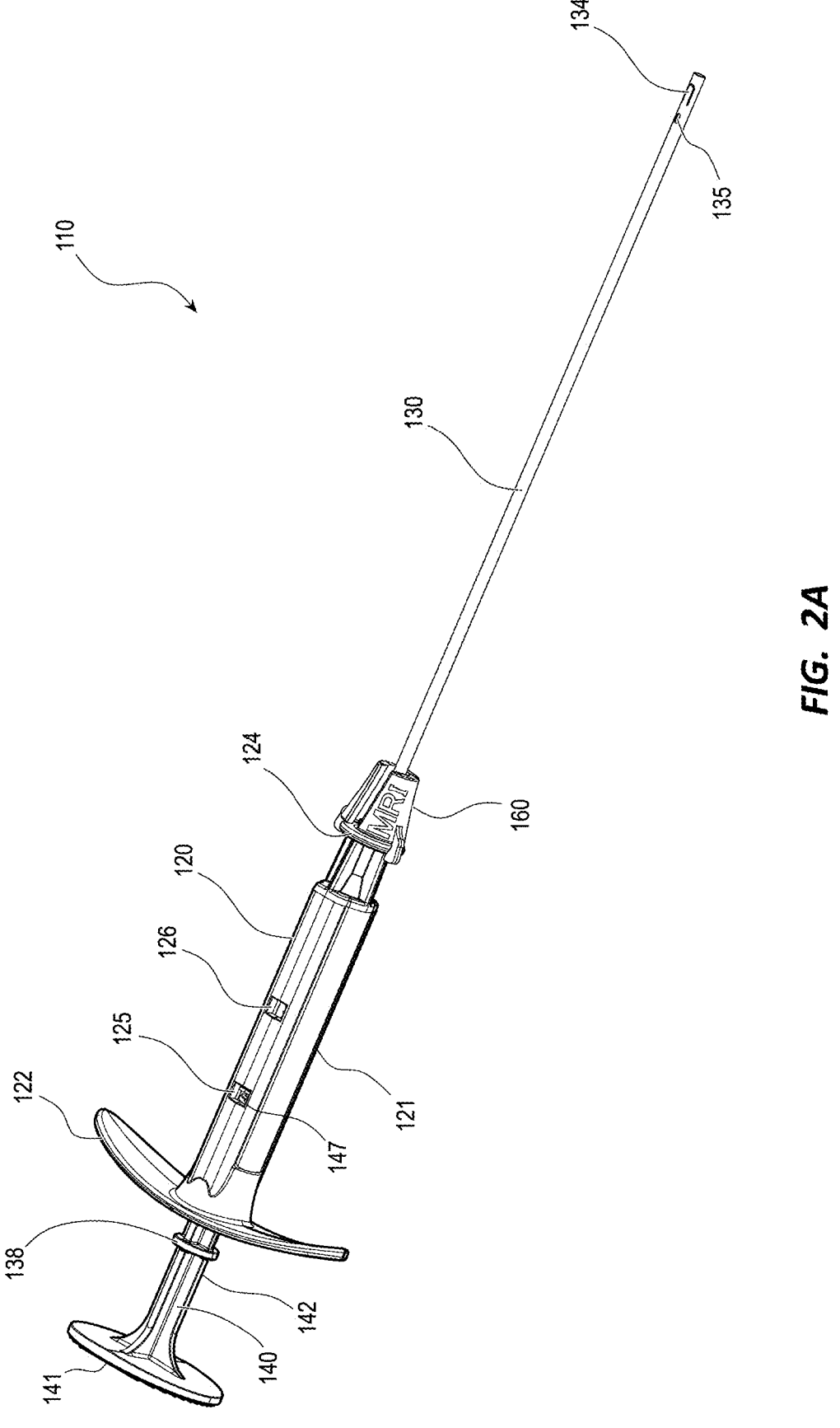
FIG. 2A is a perspective view of an embodiment of the delivery device of the deployment system of FIG. 1 in a ready-to-deploy state.
Figure 2B:
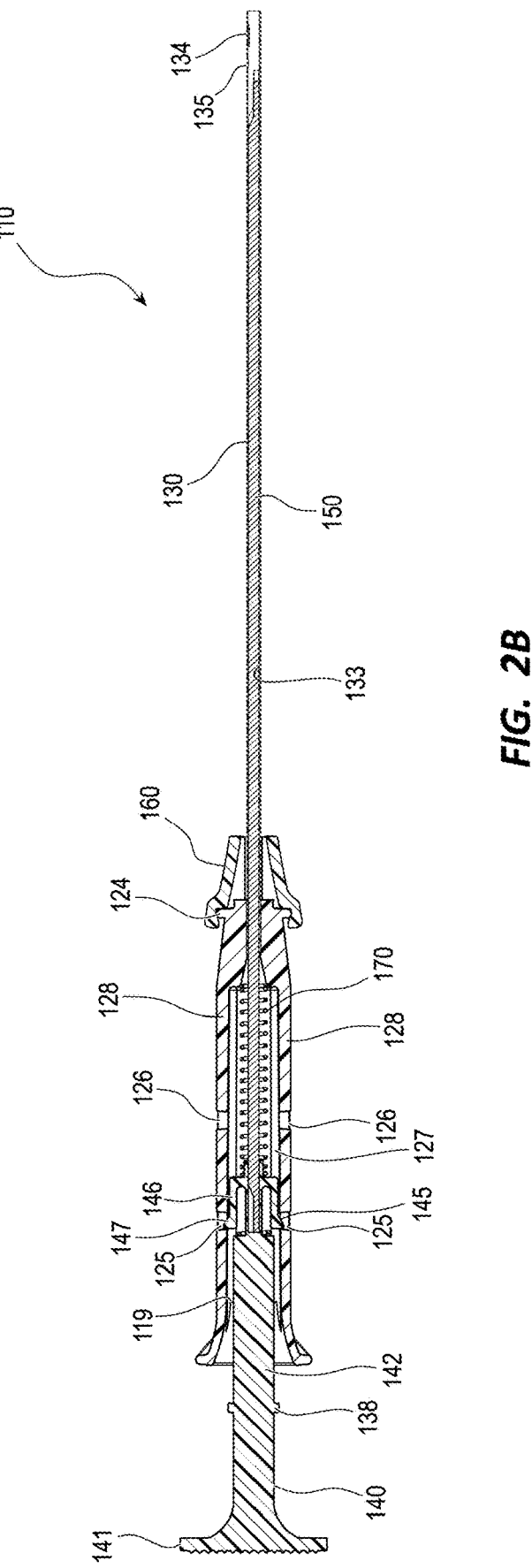
FIG. 2B is a cross-sectional view of the delivery device of FIG. 2A.
Figure 3A:
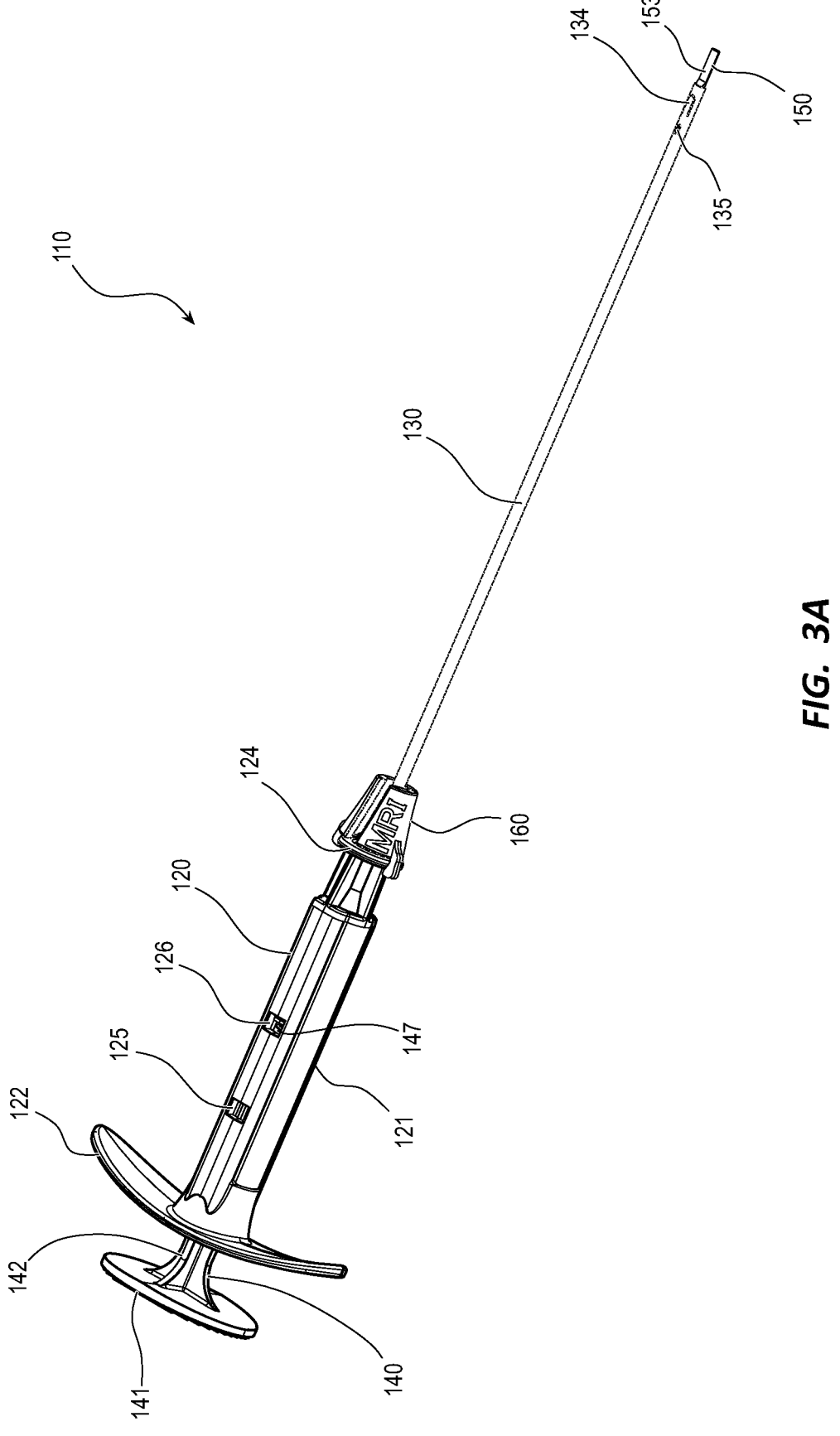
FIG. 3A is a perspective view of an embodiment of the delivery device of FIG. 1 in a deployed state.
Figure 3B:
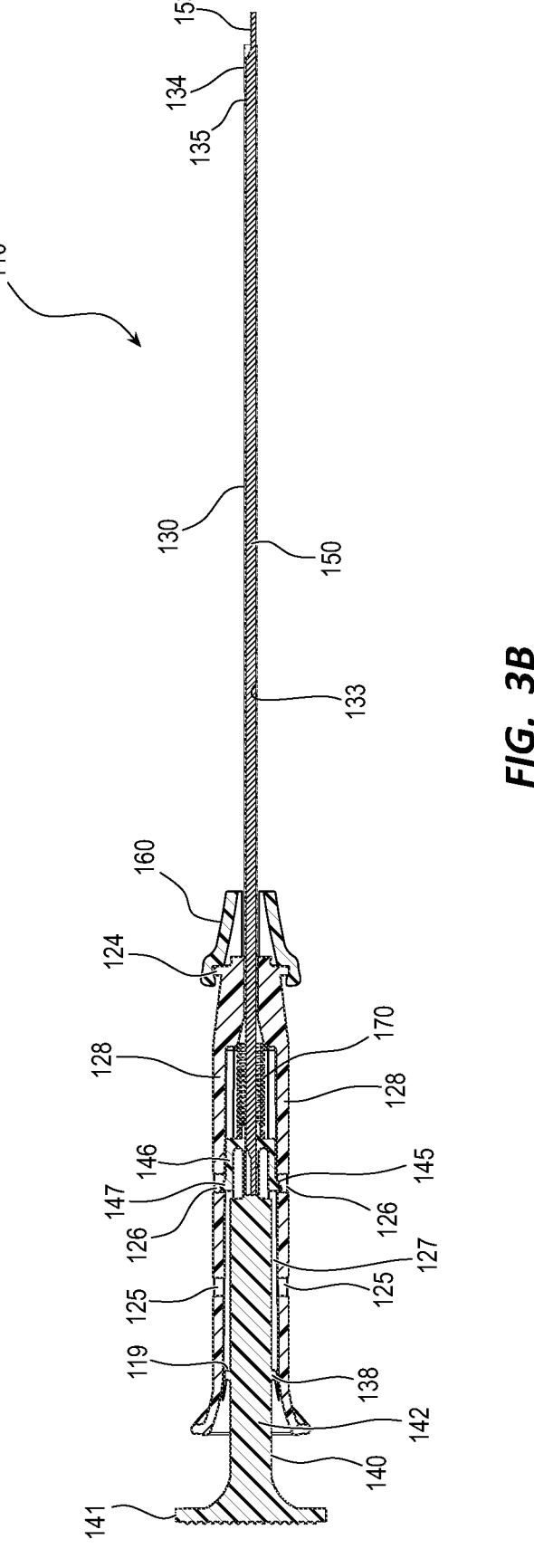
FIG. 3B is a cross-sectional view of the delivery device of FIG. 3A.

FIGS. 2A-3B illustrate an embodiment of the delivery device 110. FIGS. 2A and 2B depict the delivery device 110 in a ready-to-deploy state, and FIGS. 3A and 3B depict the delivery device 110 in a deployed state. As illustrated in FIGS. 2A-3B, the delivery device 110 includes a handle 120, a cannula 130, a plunger 140, a deployment rod 150, and a resilient member 170. The handle 120 includes a barrel 121 having a bore 127 disposed therethrough. Finger grips 122 are disposed at a proximal end of the barrel 121. As depicted, the finger grips 122 include radial outwardly extending opposing protrusions configured for placement of at least one finger of a user's hand. In other embodiments, the finger grips 122 can be of any suitable form to facilitate handling of the delivery device 110 during use. A flange 124 is disposed at a distal end of the barrel 121 for coupling of the spacer 160 when the spacer 160 is needed for a procedure.

Ready-to-deploy or proximal detents 125 are disposed in the barrel 121. As depicted, the proximal detents 125 are openings or windows in the barrel 121 disposed at 180 degrees from each other. In some embodiments, the proximal detents 125 can be of any suitable form to selectively engage with a catch 147 of the plunger 140 as will be described below. A distal lock or distal detents 126 are disposed in the barrel 121. The distal detents 126 are longitudinally spaced from and in axial alignment with the proximal detents 125. As depicted, the distal detents 126 are openings or windows in the barrel 121 disposed at 180 degrees from each other. In certain embodiments, the proximal detents 125 can be of any suitable form to selectively engage with the plunger 140 as will be described below.

The bore 127 includes opposing longitudinal channels 128. The channels 128 can receive the plunger 140 and prevent rotation of the plunger 140 relative to the barrel 121 when the plunger 140 is displaced longitudinally within the barrel 121. The proximal and distal detents 125, 126 are in communication with the channels 128. A plunger stop 119 is disposed at a proximal end of the bore 127 to engage with a stop ring 138 of the plunger 140. When the plunger stop 119 is engaged with the stop ring 138, the plunger 140 is prevented from proximal displacement relative to the handle 120.

The cannula 130 is fixedly coupled to a distal end of the handle 120. A lumen 133 of the cannula 130 is in communication with the bore 127 of the handle 120. The cannula 130 includes a retention tab 134 disposed adjacent or near a distal end of the cannula 130. The retention tab 134 can be deflected or bent inwardly when the localization device 180 is loaded into the lumen 133. When deflected, the retention tab 134 can prevent the localization device 180 from unintentionally being displaced from the cannula 130. When the localization device 180 is deployed, the retention tab 134 can be deflected upward by the localization device 180 as the localization device 180 is longitudinally displaced allowing the localization device 180 to be deployed from the cannula 130. A cannula window 135 is disposed adjacent to the retention tab 134. The cannula window 135 is in communication with the lumen 133 and allows visualization of the localization device 180 to confirm placement of the localization device 180 within the cannula 130 following assembly during manufacture of the delivery device 110 and/or prior to deployment of the localization device 180 by a user.

The plunger 140 includes a finger pad or proximal flange 141, an elongate body 142, and biased engagement members 145. The proximal flange 141 is disposed at a proximal end of the elongate body 142. As depicted, the proximal flange 141 is in the form of a disc having grip enhancing features (e.g., ridges) to facilitate longitudinal displacement of the plunger 140 by a user's finger (e.g., thumb). Other forms of the proximal flange 141 are within the scope of this disclosure. For example, the proximal flange 141 can be in the form of a ring. The elongate body 142 extends distally from the proximal flange 141. The biased engagement members 145 are disposed near or adjacent a distal portion of the elongate body 142. The biased engagement members 145 include biased cantilever arms 146 and catches 147 disposed at a free end of the cantilever arms 146. The biased cantilever arms 146 bias the catches 147 outwardly. The catches 147 include a square proximal face and a ramped distal face. The proximal face is oriented substantially perpendicular to a longitudinal axis of the plunger 140 and the distal face includes a ramp surface. The proximal face engages with a proximal wall of the proximal and distal detents 125, 126 to maintain the delivery device 110 in either the ready-to-deploy state or the deployed state. The ramped distal face engages with a distal wall of the proximal detents 125 when a distally directed force is applied to the plunger 140 to disengage the catches 147 from the proximal detents 125 and transition the delivery device 110 from the ready-to-deploy state to the deployed state.

The deployment rod 150 is fixedly coupled to the elongate body 142 of the plunger 140. The deployment rod 150 is slidingly and co-axially disposed within the lumen 133 of the cannula 130. The deployment rod 150 includes a cut-away portion 153 at a distal end. The cut-away portion 153 can apply a distally directed force to the localization device 180 when deployed.

The resilient member 170 is disposed within the barrel 121 between a distal end of the bore 127 and the distal end of the elongate body 142. The resilient member 170 can apply a proximally directed force to the plunger 140 to maintain the delivery device 110 in either the ready-to-deploy state or the deployed state. When the resilient member 170 applies the proximally directed force, the perpendicular proximal faces of the catches 147 can be forced against the proximal wall of the proximal and distal detents 125, 126 to prevent the catches 147 from disengaging from the proximal and distal detents 125, 126. As depicted, the resilient member 170 is a compression coil spring. In other embodiments, the resilient member 170 can be of any suitable form to apply a proximally directed force to the plunger 140. For example, the resilient member 170 can be an elastomer cylinder formed from elastomeric materials, such as rubber, latex, thermoplastic elastomers, etc.

In the ready-to-deploy state, as shown in FIGS. 2A and 2B, the plunger 140 of the delivery device 110 is disposed within the barrel 121 of the handle 120 such that the biased cantilever arms 146 are received in the channels 128. The catches 147 are engaged with the proximal detents 125. The resilient member 170 applies a proximally directed force to the plunger 140 to force the proximal faces of the catches 147 against the proximal wall of the proximal detents 125. The deployment rod 150 is disposed within the cannula 130 with the distal end positioned proximal to the distal end of the cannula 130.

When transitioning the delivery device 110 from the ready-to-deploy state to the deployed state, a distally directed force is applied to the proximal flange 141 of the plunger 140 to distally displace the plunger 140 and the deployment rod 150. When the plunger 140 is distally displaced, the ramped distal face of the catches 147 engage the distal wall of the proximal detents 125 causing the biased cantilever arms 146 to be deflected inwardly and the catches 147 to be disengaged from the proximal detents 125. Displacement of the plunger 140 continues until the catches 147 reach the distal detents 126 and the biased cantilever arms 146 bias the catches 147 into engagement with the distal detents 126. Upon engagement of the catches 147 with the distal detents 126, a tactile, audible, and/or visual feedback is provided to the user to indicate the delivery device 110 is in the deployed state. For example, the tactile feedback can be an increase in resistance to displace the plunger 140, the audible feedback can be a click as the catches 147 are snapped into the distal detents 126, and the visual feedback can be visualization of the catches 147 within the distal detents 126. Other forms of feedback are contemplated.

In the deployed state, as shown in FIGS. 3A and 3B, the plunger 140 of the delivery device 110 is disposed within the barrel 121 of the handle 120 such that the biased cantilever arms 146 are received in the channels 128. The catches 147 are engaged with the distal detents 126. The resilient member 170 applies a proximally directed force to the plunger 140 to force the proximal faces of the catches 147 against the proximal wall of the distal detents 126. The deployment rod 150 is disposed within the cannula 130 with the distal end extending from the distal end of the cannula 130.

Figure 4:
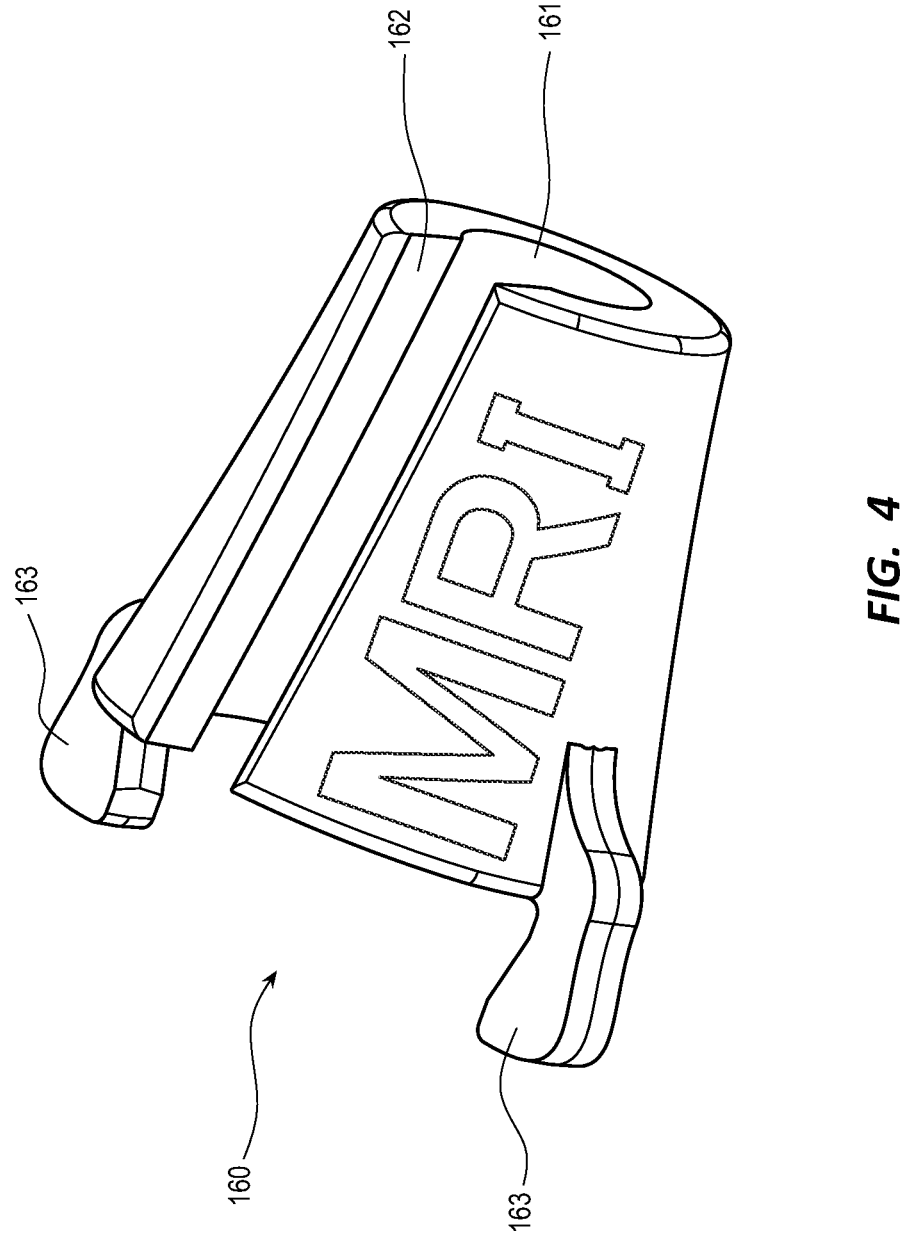
FIG. 4 is a perspective view of an embodiment of the spacer of the localization device deployment system of FIG. 1.
Figure 5A:
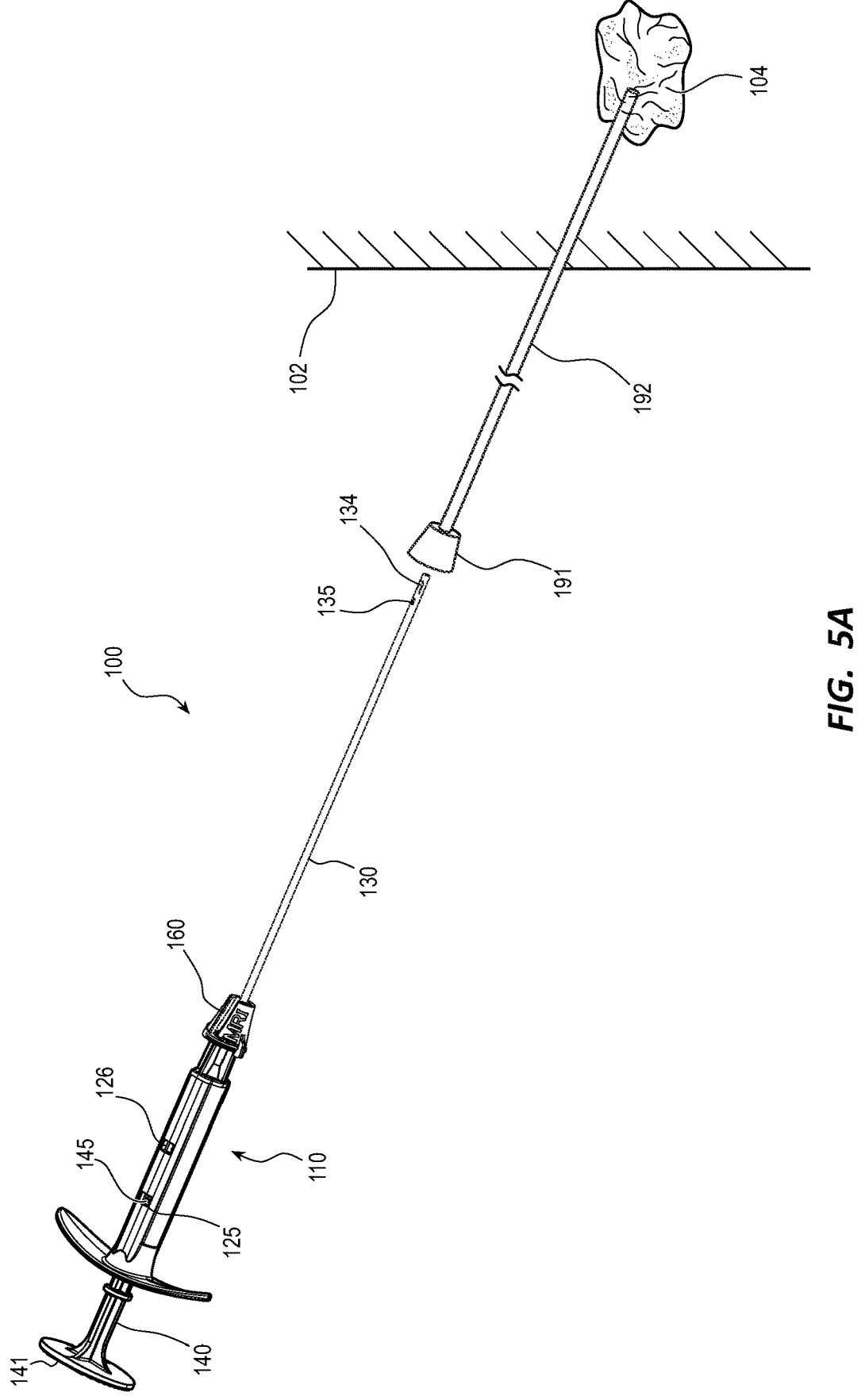
FIG. 5A is a perspective view of the localization device deployment system of FIG. 1 in use in a ready-to-deploy state.
Figure 5B:
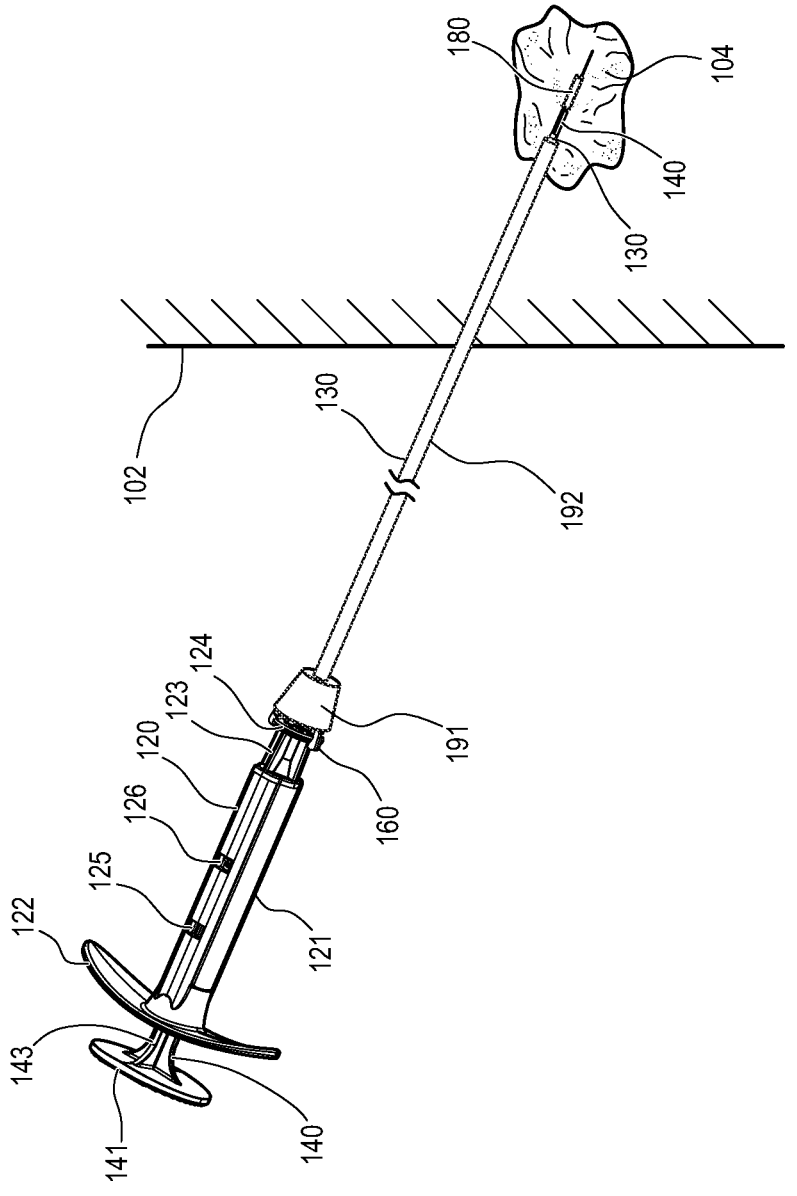
FIG. 5B is a perspective view of the localization device deployment system of FIG. 1 in use in a deployed state.
Figure 6:
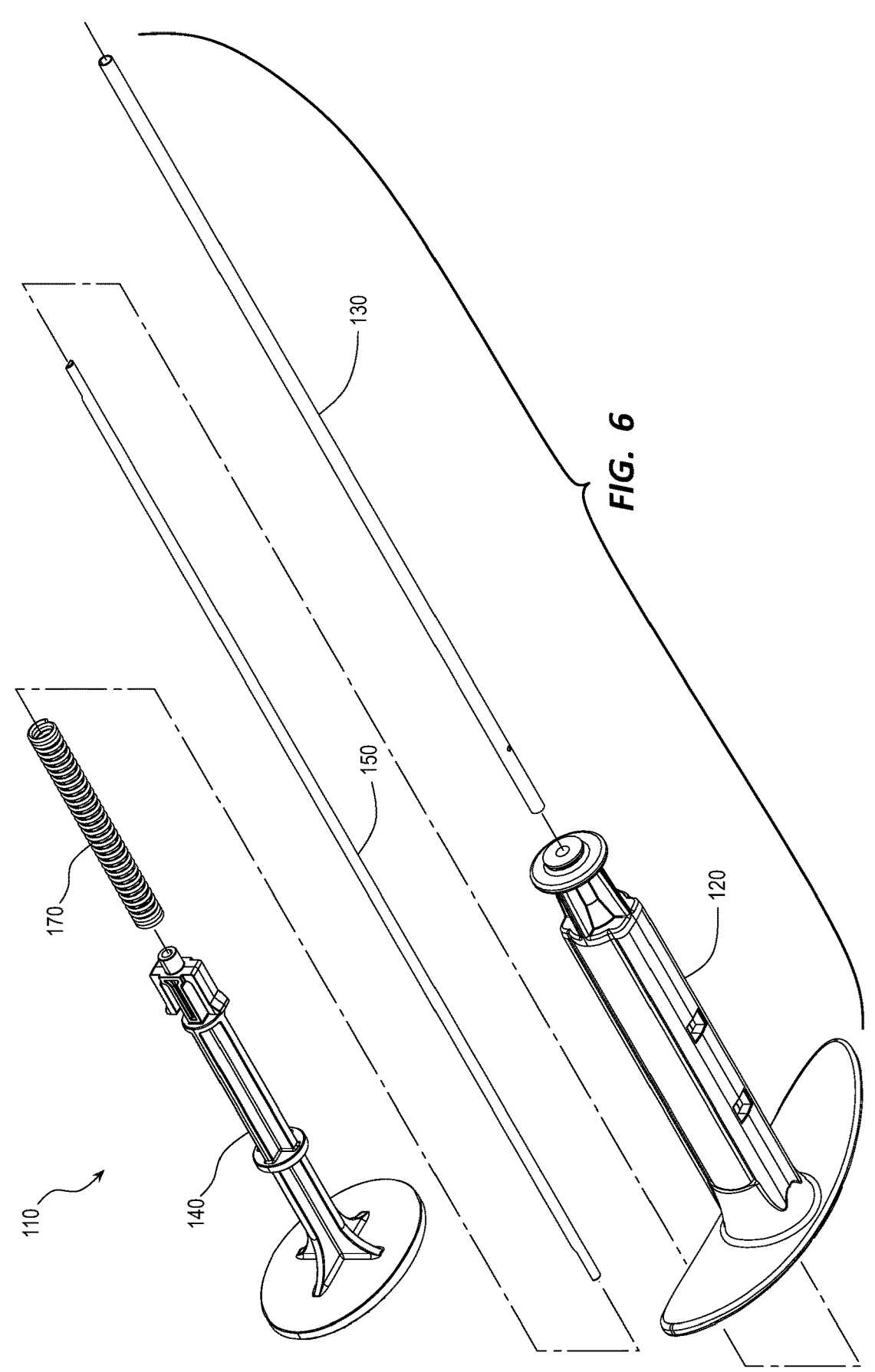
FIG. 6 is a perspective exploded view of the delivery device of FIG. 1.
Figure 7:
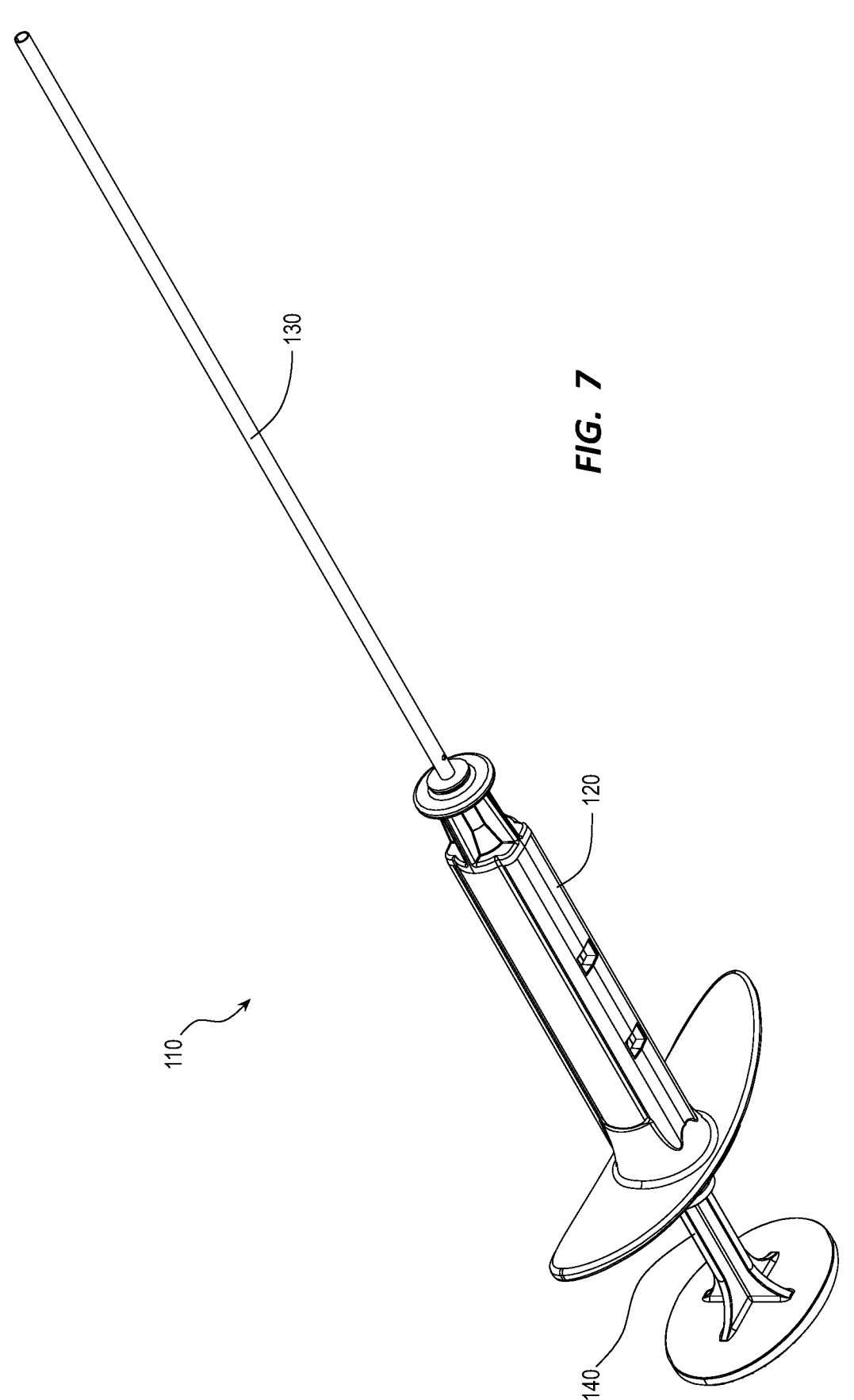
FIG. 7 is a bottom perspective view of the delivery device of FIG. 1.
Figure 8:
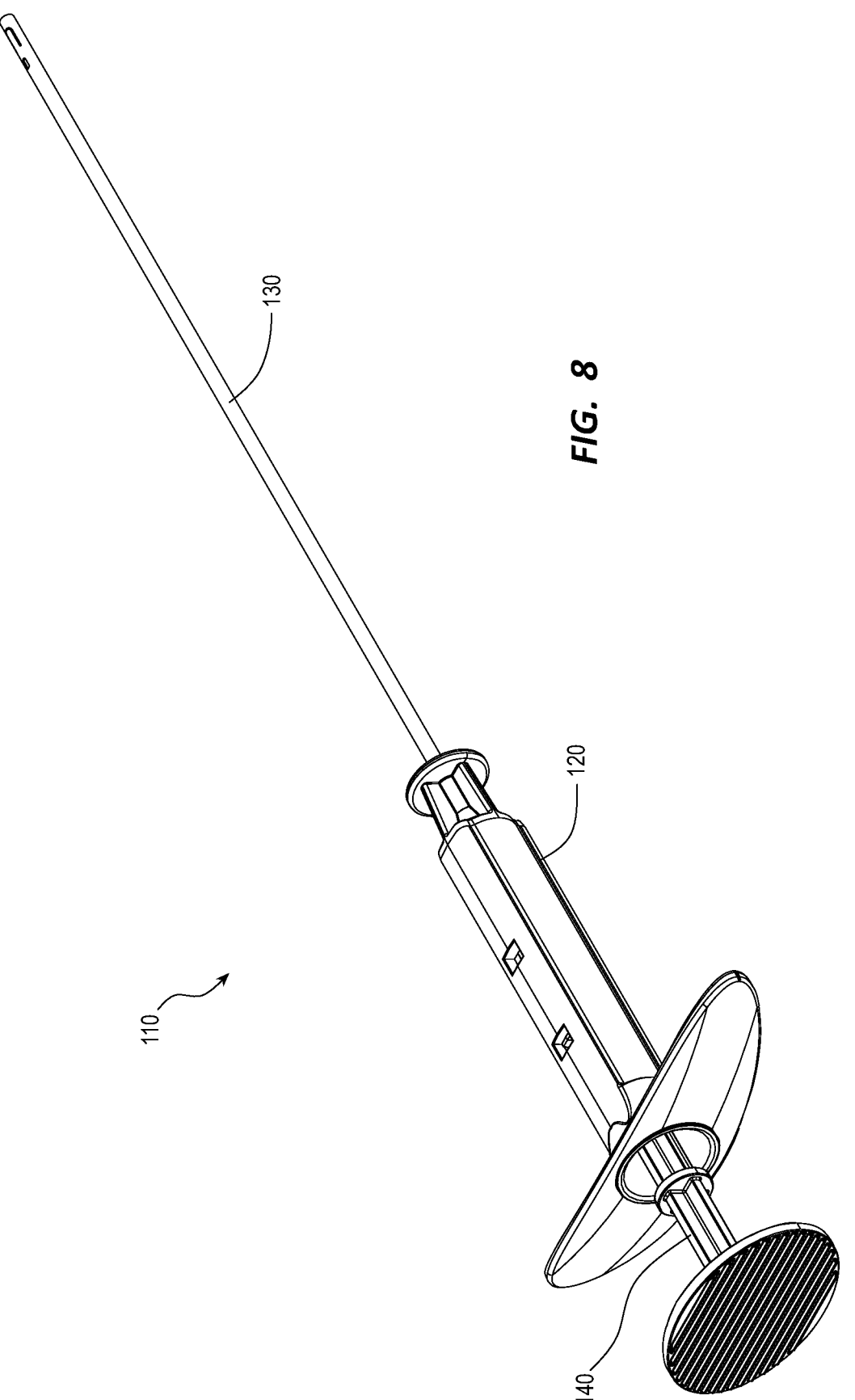
FIG. 8 is a top perspective view of the delivery device of FIG. 1.
Figures 9, 10:
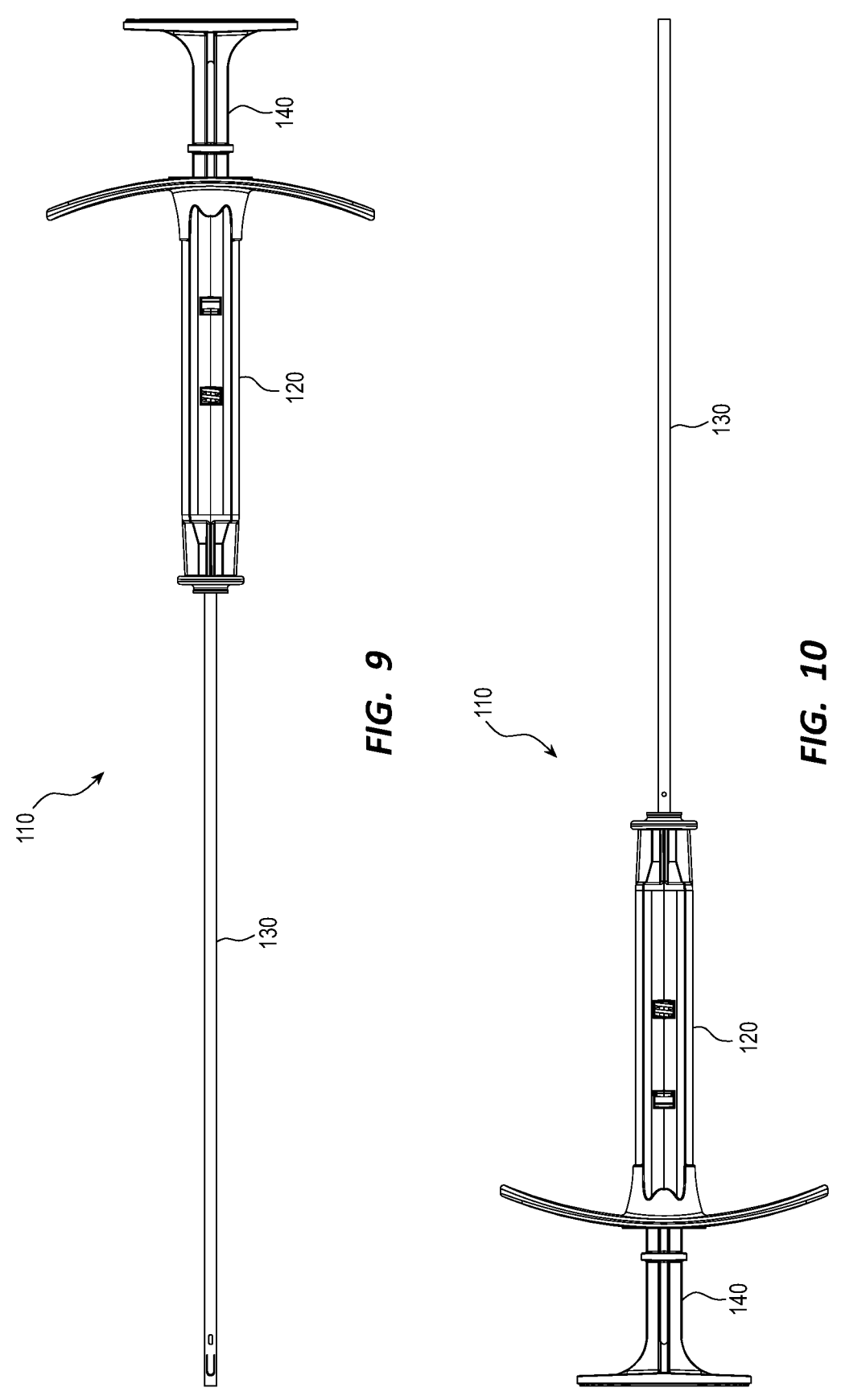
FIG. 9 is a top view of the delivery device of FIG. 1.
FIG. 10 is a bottom view of the delivery device of FIG. 1.
Figures 11, 12:
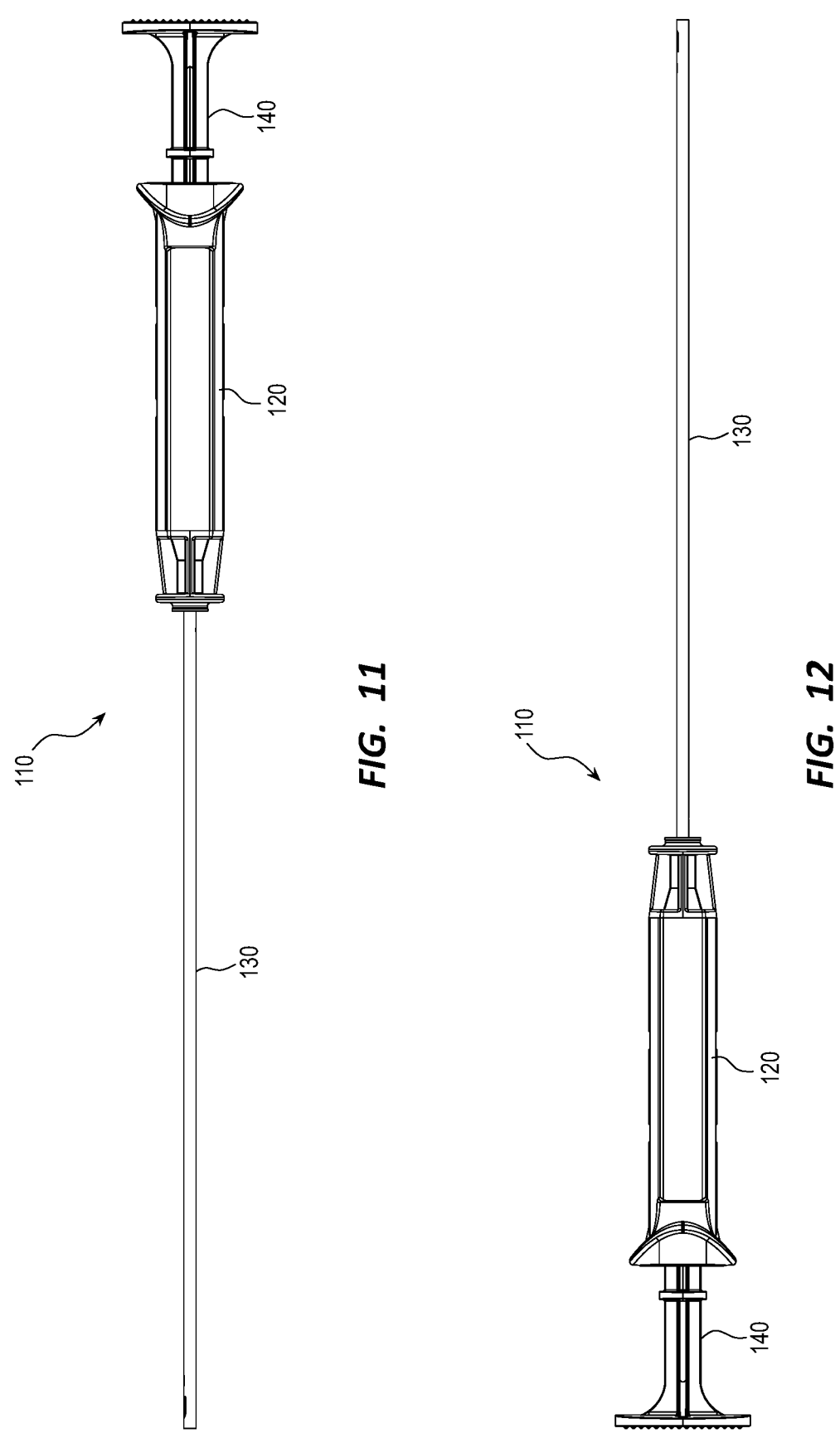
FIG. 11 is a left side view of the delivery device of FIG. 1.
FIG. 12 is a right side view of the delivery device of FIG. 1.
Figures 13, 14:
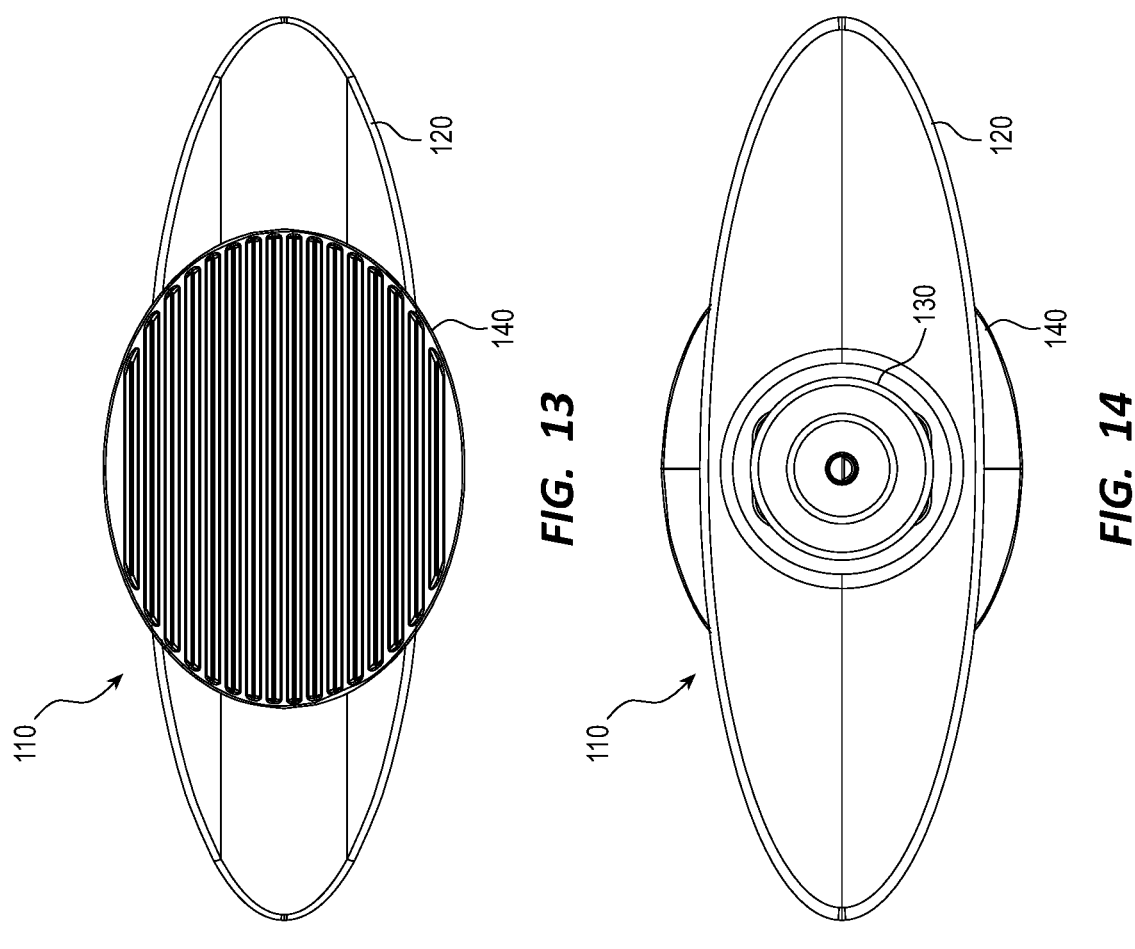
FIG. 13 is a proximal end view of the delivery device of FIG. 1.
FIG. 14 is a distal end view of the delivery device of FIG. 1.
Figure 16:
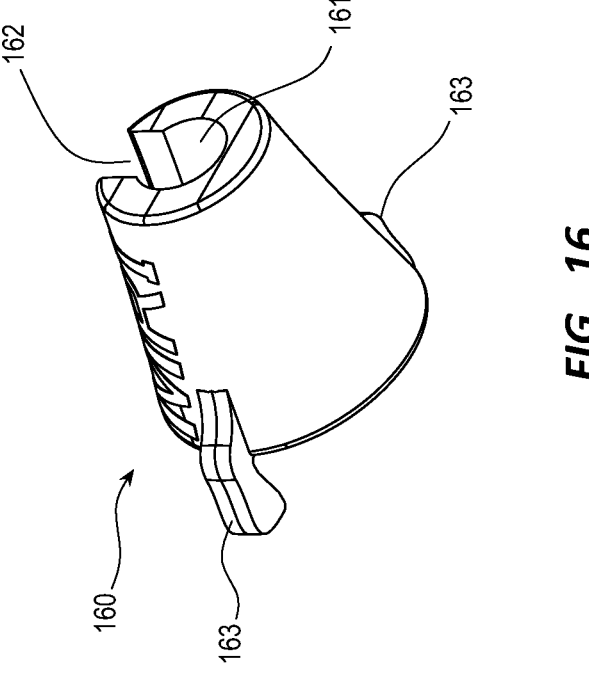
FIG. 16 is a bottom perspective view of the spacer of FIG. 1.
Figure 15:
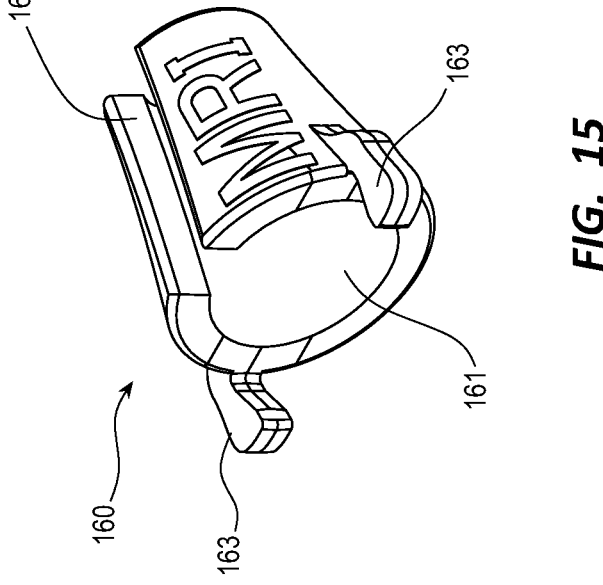
FIG. 15 is a top perspective view of the spacer of FIG. 1.
Figures 17, 18, 19, 20, 21, 22:
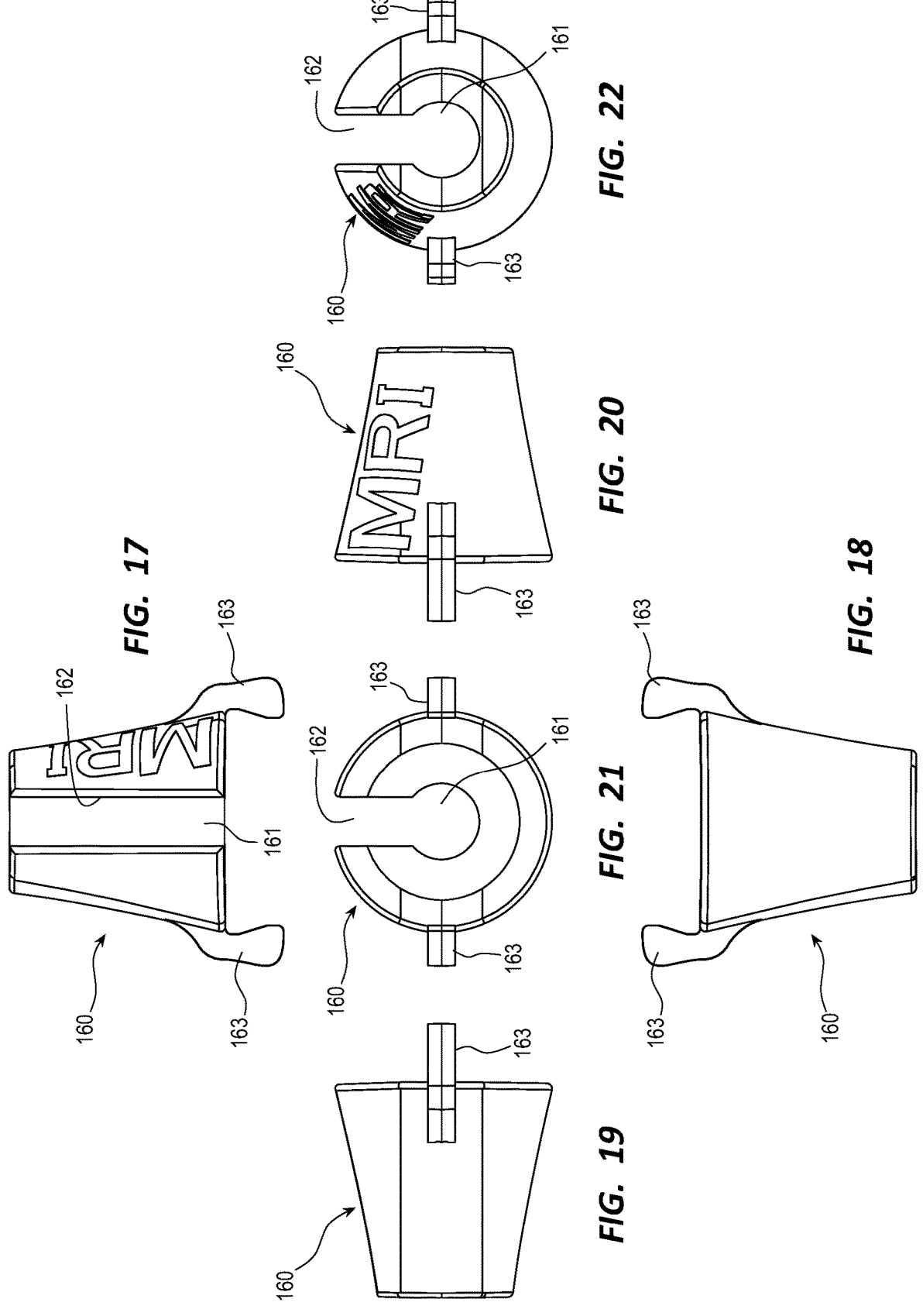
FIG. 17 is a top view of the spacer of FIG. 1.
FIG. 18 is a bottom view of the spacer of FIG. 1.
FIG. 19 is a left side view of the spacer of FIG. 1.
FIG. 20 is a right side view of the spacer of FIG. 1.
FIG. 21 is proximal end view of the spacer of FIG. 1.
FIG. 22 is a distal end view of the spacer of FIG. 1.

FIG. 4 illustrates an embodiment of the spacer 160. The spacer 160 is selectively coupleable to the delivery device 110 to adjust a length of the cannula 130 relative to a length of the sheath introducer 190. Said another way, the spacer 160 can be coupled to the delivery device 110 to effectively shorten the length of the cannula 130 relative to the sheath introducer 190 by a length of the spacer 160. For example, if the cannula 130 is one centimeter longer than a length of the sheath introducer 190 allows, a spacer 160 having a length of one centimeter can be disposed between the handle 120 and the hub 191 of the sheath introducer 190 to effectively shorten the length of the cannula 130 such that a distal end of the cannula 130 is one centimeter closer to a distal end of the sheath introducer 190. This configuration can allow use of the delivery device 110 with sheath introducers having a variety of lengths.

As illustrated in FIG. 4, the spacer 160 includes a body 161, a slot 162, and fingers 163. The body 161 is conical shaped. Other shapes are contemplated. The slot 162 extends through the body 161 to allow the cannula 130 to pass laterally through the slot 162 as the spacer 160 is coupled to the handle 120. The fingers 163 extend proximally from the body 161 to selectively engage with the flange 124 of the handle 120 when the spacer 160 is coupled to the handle 120.

FIGS. 5A and 5B illustrate the deployment system 100 in use to deploy a localization device 180 into a target lesion. As illustrated, the sheath introducer 190 is disposed through a skin 102 of a patient such that a distal end of the tubular sheath 192 is positioned within a target lesion 104. In some embodiments, the sheath introducer 190 may be inserted into the target lesion 104 as a step of a stereotactic or MRI guided biopsy procedure and a biopsy device removed from the sheath introducer 190 to provide access to the target lesion 104 by the delivery device 110. In other embodiments, the sheath introducer 190 may be percutaneously inserted over a needle or trocar and the needle or trocar removed to provide access to the target lesion 104 by the delivery device 110.

The delivery device 110 is shown in FIG. 5A in the ready-to-deploy state with the biased engagement members 145 engaged with the proximal detents 125. The localization device 180 is disposed in the cannula 130. The retention tab 134 is deflected inwardly to retain the localization device 180 within the cannula 130. The localization device 180 can be visualized through the cannula window 135 to confirm its presence and position in the cannula 130. Optionally, the spacer 160 can be coupled to the handle 120 to effectively shorten the length of the cannula 130 to accommodate the length of the sheath introducer 190.

The delivery device 110 is shown in FIG. 5B in the deployed state. When the delivery device 110 is transitioned from the ready-to-deploy state to the deployed state, a distally directed force is applied to the plunger 140 to distally displace the plunger 140 relative to the handle 120. When the plunger 140 is distally displaced, the biased engagement members 145 disengage from the proximal detents 125 and reengage with the distal detents 126. The deployment rod 150 is distally displaced to apply a distally directed force to the localization device 180 to distally displace or deploy the localization device 180 from the cannula 130 into the target lesion 104. The localization device 180 can be deployed from the cannula 130 in axial alignment with the cannula 130. When the localization device 180 is distally displaced, the retention tab 134 is deflected outwardly by the localization device 180.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of an localization device may include one or more of the following steps: positioning a distal portion of a delivery device within a target lesion; transitioning the delivery device from a ready-to-deploy state to a deployed state, wherein a plunger of the delivery device is displaced from engagement with a ready-to-deploy detent of the delivery device to engagement with a deployed detent of the delivery device; and deploying an localization device from the delivery device into the target lesion. Other steps are also contemplated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

In the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest to the practitioner during use.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

The terms "a" and "an" can be described as one, but not limited to one. For example, although the disclosure may recite a housing having "a stopper," the disclosure also contemplates that the housing can have two or more stoppers.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A delivery device to deliver a localization device, comprising:
   a handle to be gripped by a user and comprising:
     a bore defined by a wall of the handle;
     a proximal detent extending through the wall of the handle; and
     a distal detent extending through the wall of the handle, wherein the distal detent is longitudinally spaced from the proximal detent;
   a cannula coupled to the handle and comprising a lumen;
   a plunger slidingly disposed within the bore of the handle and comprising an outwardly biased engagement member comprising:
     a cantilever arm; and
     a catch disposed at an end of the cantilever arm, the catch configured to engage with the proximal detent and the distal detent; and
   a deployment rod coupled to the plunger and co-axially disposed within the lumen of the cannula.

2. The delivery device of claim 1, wherein the delivery device further comprises a resilient member disposed within the handle to apply a proximally-directed force to the plunger.

3. The delivery device of claim 1, wherein the delivery device further comprises a spacer selectively couplable to a distal end of the handle to effectively shorten a length of the cannula.

4. The delivery device of claim 1, wherein the proximal and distal detents comprise windows through the wall to allow visualization of the biased engagement member when the biased engagement member is engaged with the proximal and distal detents.

5. The delivery device of claim 1, wherein the cannula comprises:
   a retention tab disposed proximal to a distal end of the cannula to retain the localization device within the lumen of the cannula prior to deployment of the localization device from the delivery device; and
   a cannula window disposed proximal to the retention tab to allow visualization of the localization device within the lumen of the cannula prior to deployment of the localization device from the delivery device.

6. The delivery device of claim 1, wherein the biased engagement member comprises:

the cantilever arm coupled to an elongate body; and the catch disposed at a proximal end of the cantilever arm to engage with the proximal and distal detents of the handle, wherein the catch comprises:

a distal face oriented at an angle to a longitudinal axis of the elongate body to prevent the plunger from being distally displaced; and a proximal face oriented perpendicular relative to the longitudinal axis of the elongate body to allow the plunger to be displaced from engagement with the proximal detent to engagement with the distal detent.

7. The delivery device of claim 1, wherein the delivery device is in a ready-to-deploy state when the biased engagement member is engaged with the proximal detent, and wherein the delivery device is in a deployed state when the biased engagement member is engaged with the distal detent.

8. The delivery device of claim 1, wherein the localization device is deployed from the delivery device in axial alignment with the delivery device.

9. The delivery device of claim 2, wherein the proximally-directed force applied to the plunger is configured to cooperate with an outward force applied by the outwardly biased engagement member so as to maintain engagement of the catch with the proximal detent or the distal detent.

10. The delivery device of claim 1, further comprising a resilient member configured to apply a proximally-directed force to the plunger such that the catch is prevented from disengaging with the proximal detent or the distal detent.

\* \* \* \* \*